United States Patent [19]
Jones

[11] Patent Number: 4,904,471
[45] Date of Patent: Feb. 27, 1990

[54] PREPARATION FOR TREATMENT OF HUMAN HAIR AND SKIN AND METHOD OF USING SAME

[76] Inventor: Angie L. Jones, 75-95 Clinton Ave., Newark, N.J. 07114

[21] Appl. No.: 72,489

[22] Filed: Jul. 13, 1987

Related U.S. Application Data

[63] Continuation-in-part of Ser. No. 896,900, Aug. 15, 1986, abandoned, which is a continuation-in-part of Ser. No. 884,469, Jul. 11, 1986, abandoned.

[51] Int. Cl.⁴ .............................................. A61K 7/075
[52] U.S. Cl. .................................... 424/195.1; 424/74
[58] Field of Search ............................... 424/195.1, 74

[56] References Cited

U.S. PATENT DOCUMENTS

| | | | |
|---|---|---|---|
| 4,139,619 | 2/1979 | Chidsey | 424/45 |
| 4,331,611 | 5/1982 | Mookherjee et al. | 260/464 |

FOREIGN PATENT DOCUMENTS

| | | | |
|---|---|---|---|
| 1617520 | 5/1972 | Fed. Rep. of Germany | 424/74 |
| 3301575 | 7/1984 | Fed. Rep. of Germany | 424/74 |
| 2378512 | 9/1978 | France | 424/74 |
| 2510402 | 2/1983 | France | 424/74 |

OTHER PUBLICATIONS

Sagarin, Cosmetics, Interscience Publishers, Inc., 1957, pp. 552–567, 756–763.

*Primary Examiner*—William R. Dixon, Jr.
*Assistant Examiner*—Ellen M. McAvoy
*Attorney, Agent, or Firm*—Millen, White & Zelano

[57] ABSTRACT

A preparation for the treatment of hair, scalp and skin utilizes as a basic ingredient petroleum-based heavy mineral oil. The heavy mineral oil is utilized as a hair treatment preparation on a continuous basis and results in control of dandruff and split ends while promoting the growth of healthy hair. In addition, the preparation provides the hair with body, fullness and sheen while strengthening the hair shafts so as to minimize breakage while at the same time not appearing greasy. In a preferred embodiment, the preparation includes herbal fragrance oils and oils extracted from burdock root, nettles and sage.

7 Claims, No Drawings

PREPARATION FOR TREATMENT OF HUMAN HAIR AND SKIN AND METHOD OF USING SAME

BACKGROUND OF THE INVENTION

This application is a C-I-P of U.S. Patent Application Ser. No. 896,900, filed Aug. 15, 1986, abandoned, which is in turn a C-I-P of U.S. Patent Application Ser. No. 884,469, filed July 11, 1986, abandoned, titled "Preparation for Treatment of Hair and Skin".

FIELD OF THE INVENTION

The instant invention relates to preparations for treatment of hair, scalp and skin. More particularly, the instant invention relates to preparations for the treatment of hair and skin and to treatment of hair and skin utilizing the preparations.

Generally, light mineral oil is being used for topical treatment of hair and skin. However, light mineral oil is not absorbed readily by either the skin, hair follicles or hair shafts. Rather, light mineral oil tends to remain on the surface and simply creates a greasy film. Since light mineral oil does not penetrate surface areas of hair and skin, light mineral oil does not treat these areas by entering the interstices between the deceased cells which form hair and the outer layer of the epidermis. Accordingly, light mineral oil does not adequately provide subsurface lubrication so as to replace natural oils in the skin, scalp and hair and to thereby promote control of dryness in the skin and scalp, control of split ends in hair shafts and promote the general health of one's scalp which leads to the healthy growth of hair.

Many hair preparations are in essence grease with mixtures of chemical synthetics that weigh down hair shafts and cause the shafts to temporarily adhere to one another resulting in limp, obviously greasy hair that is considered just generally unattractive by most people.

OBJECT OF THE INVENTION

In view of the foregoing considerations, it is an object of the instant invention to provide a new and improved human hair, scalp and skin preparation and new uses thereof for lubricating skin and strengthening hair shafts as well as creating conditions for the growth of healthy hair.

Upon further study of the specification and appended claims, further objects and advantages of this invention will become apparent to those skilled in the art.

SUMMARY OF THE INVENTION

The instant invention contemplates a preparation for use on the skin, scalp and human hair wherein the preparation comprises heavy mineral oil, natural extract oil of burdock root and herbal fragrance, the heavy mineral oil comprising at least 90% by volume of the preparation. The instant invention further comprises using the preparation for the treatment of hair wherein the hair is treated continually on at least a daily basis in order to maintain the health of hair follicles and the strength of hair shafts so as to promote hair growth and softness while preventing falling hair, breakage and split ends.

The instant invention further contemplates adding the natural oil extract of nettles and the natural oil extract of sage to the mineral oil and natural oil extract of burdock root in relatively small amounts by volume with respect to the heavy mineral oil.

DESCRIPTION OF THE PREFERRED EMBODIMENTS

The instant invention utilizes heavy mineral oil as the primary ingredient of a preparation for the treatment of hair, scalp and skin of humans. In the past, light mineral oil is used as a scalp and hair treatment preparation. By heavy mineral oil, the inventor is referring to the heavy petroleum based oil which is extracted subsequent to the extraction of light mineral oil in the petroleum cracking process and prior to the extraction of petroleum jelly. Heavy mineral oil is widely used as a laxative and is available from many sources such as, for example, E.R. Squibb & Sons, Inc. of Princeton, N.J. and Grey Drug Fair, Inc. of Cleveland, Ohio. Light mineral oil has long been used for hair preparation, but has the disadvantages set forth in the foregoing discussion of the prior art.

Preferably, the heavy mineral oil is applied on a daily basis and may be used as frequently as twice a day. It has been found that the advantageous effects of utilizing heavy mineral oil become evident after approximately two weeks of use and continue thereafter as long as the heavy mineral oil is used. It has been found that the heavy mineral oil controls dandruff and dryness, controls split ends and promotes healthy hair growth Moreover, the hair is non-greasy, soft and has sufficient resilience to remain fluffy and bouncy so as to hold style.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLES OF PREPARATION

The actual preparation is preferably a mixture of petroleum-based heavy mineral oil, and extract oils of nettles, sage and jasmine. In accordance with a preferred embodiment of the invention, the preparation is made with the following measurements:

Example I

Heavy Mineral oil—16 fluid ounces
Jasmine oil—4 drops
Natural oil extracted from burdock root—10 drops
Natural oil extract from nettles—10 drops
Natural extract oil from sage—10 drops.
(wherein each drop is about 0.1–0.3 ml)
The above mixture is then shaken or rapidly mixed until a head of foam occurs so as to disperse the additive oils in the heavy mineral oil. The preparation is then ready for use. After the mixture has been on the shelf for a while, the oils may begin to separate. Accordingly, the preparation should be shaken prior to each use.

While the foregoing formula is preferred, the following formulas for the preparation are also within the scope of the instant invention:

Example II

Heavy mineral oil—90 fluid ounces
Herbal fragrance (natural oil extract)—10 fluid ounces

Example III

Heavy mineral oil—70 fluid ounces
Herbal fragrance (natural oil extract)—½ fluid ounce
Nettles oil (natural extract oil)—2½ fluid ounces

Example IV

Heavy mineral oil—6 fluid ounces
Herbal fragrance (natural extract oil)—1 fluid ounce
Nettles oil (natural extract oil)—2 fluid ounces burdock root
Burdock root oil (natural extract oil)—1 fluid ounce Heavy mineral oil is the base ingredient of each above cited formula. No preservatives or chemical additives are utilized in that the heavy mineral oil includes natural preservation properties. In that heavy mineral oils are sold with an expiration date, the expiration date is adhered to and in accordance with the invention any preparation remaining after the expiration date is disposed of.

Preferably the heavy mineral oil used in each of the foregoing examples is known as DRAKEOL No. 35 mineral oil available from the Peneco Division of the Pennzoil Corporation of Lindhurst, N.J. 07071.

In the above examples, the oil of nettles, oil of sage, and oil of burdock root are obtainable from the Bio-Botanica Company of Hauppange, N.Y. 11788. Each of the herb oils is obtained by a proprietary process of the Bio-Botanica Company and is identified as a pure BIO-CHELATED extract contained vegetable glycerin and grain neutral spirits at 12-14% by volume.

The Jasmine oil is a conventional product which is used as a fragrance and does not contain perfume.

EXAMPLES OF USE

Generally, the preparation is applied in the morning and at bedtime with bedtime use being more extensive in troubled areas. A small amount is applied to hair and rubbed vigorously into the hair and scalp before combing.

Small amounts of the preparation may be applied after shampooing while the hair is still wet and prior to setting. After conditioning, a small amount of the preparation is applied subsequent to rinsing and prior to setting.

The preparation is useful as a blow-drying conditioner and a hot pressing conditioner in order to minimize dryness, hair breakage and split ends when hair is treated with heat.

In place of wet hair products, the preparation can be used for curls by first dampening or lightly moistening the hair without totally wetting the hair and then applying the preparation thereto by massaging the preparation vigorously into the hair. The hair is then combed and styled.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating human hair to promote control of dryness, encourage growth of healthy hair and softness while minimizing falling hair, hair breakage and split ends, the method comprising the steps of applying a mixture comprising a petroleum-based heavy mineral oil with an effective amount of natural oil extract of burdock root to the hair and scalp on a continuous basis wherein the mineral oil is used at least every other day and wherein heavy mineral oil is massaged into the hair and scalp.

2. A method of claim 1, wherein the mixture contains a natural extract oil obtained from nettles.

3. A method of claim 2, wherein the mixture contains a natural extract oil obtained from sage.

4. A method of claim 3, wherein the mixture contains jasmine oil as a herbal fragrance oil.

5. A method of claim 1, wherein the preparation is used at a frequency of twice a day.

6. A preparation for the treatment of hair, the preparation comprising a mixture of the following ingredients: petroleum-based heavy mineral oil as a basic ingredient, jasmine oil, natural extract oil of burdock root, natural extract oil of nettles and natural extract oil of sage wherein the volumetric ratio of mineral oil to other oils is in the range of about 16 fluid ounces of mineral oil to about 0.10-0.30 milliliters each of the burdock root, sage and nettle extract oils and about 0.5-0.15 milliliters of jasmine oil.

7. A preparation for treating the hair and scalp, the preparation being a mixture comprising petroleum-based heavy mineral oil as the basic ingredient, jasmine oil and natural extract oils of nettles and an effective amount of burdock root to promote control of dryness and control split ends of hair shafts, wherein the liquid volume ratio of the ingredients is about 6 fluid ounces of heavy mineral oil, about 1 fluid ounce of natural jasmine oil and about 2 fluid ounces of natural extract oil of nettles.

* * * * *